United States Patent [19]

Jöbsis et al.

[11] 4,380,240
[45] Apr. 19, 1983

[54] APPARATUS FOR MONITORING METABOLISM IN BODY ORGANS

[75] Inventors: Frans F. Jöbsis; Johannes H. Keizer; Ronald F. Overaker, all of Durham, N.C.

[73] Assignee: Duke University, Inc., Durham, N.C.

[21] Appl. No.: 289,413

[22] Filed: Aug. 3, 1981

Related U.S. Application Data

[63] Continuation-in-part of Ser. No. 188,578, Sep. 18, 1980, Pat. No. 4,321,930, which is a continuation-in-part of Ser. No. 810,777, Jun. 28, 1977, Pat. No. 4,281,645, and Ser. No. 17,727, Mar. 5, 1979, Pat. No. 4,223,680, which is a continuation-in-part of Ser. No. 810,777, Jun. 28, 1977, Pat. No. 4,281,645.

[51] Int. Cl.³ .............................................. A61B 5/00
[52] U.S. Cl. ................................................. 128/633
[58] Field of Search .............................. 128/633–635, 128/663–665, 673, 687–689

[56] References Cited

U.S. PATENT DOCUMENTS

| | | | |
|---|---|---|---|
| 3,154,067 | 10/1964 | Stenstrom et al. | 128/687 |
| 3,167,658 | 1/1965 | Richter | 128/687 |
| 3,412,729 | 11/1968 | Smith, Jr. | 128/633 |
| 3,517,999 | 6/1970 | Weaver | 128/687 |
| 3,628,525 | 12/1971 | Polanyi et al. | 128/633 |
| 3,704,706 | 12/1972 | Herczfeld et al. | 128/633 |

Primary Examiner—William E. Kamm
Attorney, Agent, or Firm—B. B. Olive

[57] ABSTRACT

A mounting structure secures to a selected portion of the human body, e.g., the head, a limb, or the torso, and incorporates light source and light detecting means adapted for association with spectrophotometric circuitry for in situ, in vivo monitoring of local metabolism in the area of the body where the structure is secured.

5 Claims, 14 Drawing Figures

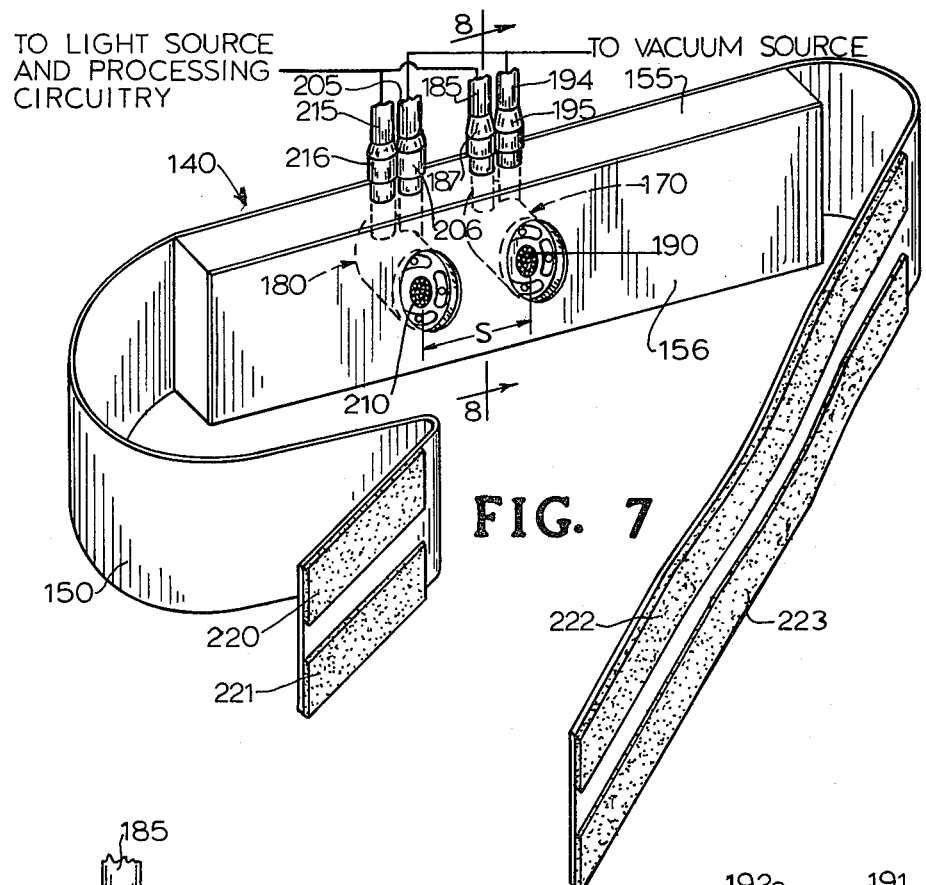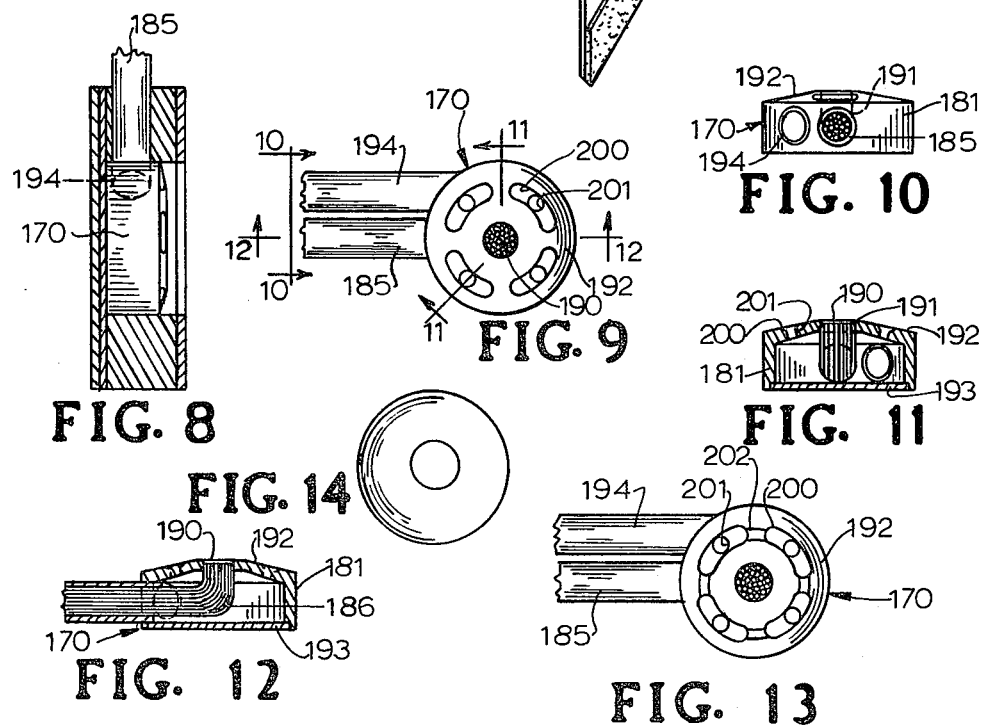

APPARATUS FOR MONITORING METABOLISM IN BODY ORGANS

The invention described herein was made in the course of work under a grant or award from the Department of Health, Education and Welfare.

CROSS REFERENCE TO RELATED APPLICATIONS AND PATENTS

This application is a continuation-in-part of application Ser. No. 188,578, filed Sept. 18, 1980, now U.S. Pat. No. 4,321,930, which, in turn, is a continuation-in-part of both application Ser. No. 810,777, filed June 28, 1977, now U.S. Pat. No. 4,281,645 and application Ser. No. 017,727, filed Mar. 5, 1979, now U.S. Pat. No. 4,223,680, the latter also being a continuation-in-part of application Ser. No. 810,777, filed June 28, 1977, now U.S. Pat. No. 4,281,645.

TECHNICAL FIELD

The invention relates to spectrophotometric apparatus for monitoring selected characteristics of the human body, in vivo.

BACKGROUND ART

In the prior patent applications there has been described a spectrophotometric method and apparatus directed to non-invasive, continuous, atraumatic, in vivo, in situ monitoring of metabolism in a body organ. In the described applications, measuring and reference wavelengths within the near-infrared region, i.e., 700–1300 nm, are utilized for non-invasive, continuous, atraumatic, in situ, in vivo monitoring of oxidative metabolism by monitoring oxygen sufficiency in an internal organ, e.g., the brain or heart, of a human or animal body. Advantage is taken of the critical characteristic of cellular enzyme cytochrome, a, $a_3$ (also known as cytochrome c oxidase and identified by EC 1.9.3.1) within the optical path and within the radiated portion of the selected organ for absorbing the selected measuring wavelength and for light of this measuring wavelength, as well as at least one reference wavelength within the same defined infrared region and at a low, non-hazardous level of intensity to be detectable at the end of a relatively long transillumination or reflectance path, e.g., of several centimeters length, which may include substantial content of bone as well as soft tissue and skin. Variations in metabolic and circulatory parameters during measuring are recognized and the selection of wavelengths, circuitry and method also provide techniques for compensating for changes in blood volume in the organ being monitored, for continuous monitoring of hemoglobin oxygenation and blood volume, for intermittent monitoring of blood flow rate, for skin blood flow effects and variations in the light source, i.e., laser diode, output.

In view of the fact that the prior art has been discussed extensively in the prior patent applications, such discussion will not be repeated here. The discussion to be found in the prior patent applications should thus be treated as incorporated herein by reference.

In the context of the mentioned prior patent applications and prior art, the present invention is primarily concerned with the light source and light detecting structure at the place of attachment to the body and with the means for mounting the light source-light detecting structure on the body. Thus, the present invention is primarily intended to provide an improvement over the light source-light detecting structure shown in copending application Ser. No. 188,578 as well as over all known prior art deemed relevant to the invention. A useful background of the prior art may be had by making reference to the discussion of the prior art in the mentioned prior patent applications and to the light source and light detecting structures described in U.S. Pat. Nos. 3,527,932; 3,674,008; 3,638,640; 3,704,706; and 4,077,399.

Taking all of the foregoing into account, further development and experimentation with the spectrophotometric apparatus and method for measuring local metabolism described in the mentioned patent applications has revealed the need for an improved means for securing and shielding the light sources as well as the light detectors when attached to the body and particularly in reference to improving the light source-detector mounting arrangement described in copending application Ser. No. 188,578. Also, a need has arisen for further simplification of the light source-light detecting structure which is attached to the body and to the associated mounting structure such that it can be made economically in a disposable form and where necessary for a single end use application such as in a surgical operation, emergency accident situations, and the like.

The achievement of these various needed improvements thus becomes the general object of the invention and other objects will be revealed as the description proceeds.

DISCLOSURE OF INVENTION

The invention is directed to improvements in means for orienting in reference to the body, supporting on and attaching to the body, and shielding from ambient light at the point of attachment the light sources and the light detectors associated with remotely located spectrophotometric apparatus utilized for monitoring local metabolism in vivo, non-invasively and atraumatically according to the teachings of the related prior patent applications previously referred to.

The invention apparatus is attached to the body, e.g., the head, a limb or to the torso, and operates with the apparatus and according to the techniques of the prior patent applications. Decisive information is provided on the parameter of oxygen sufficiency in the tissue or organ in question, in vivo. The invention apparatus when operating in conjunction with the apparatus and techniques of the prior patent applications also provides the capability of monitoring the oxygenation state of the blood being supplied, blood volume and blood flow rate in the portion of the body being monitored and in a manner which is non-invasive and atraumatic.

As distinct from the means for generating the near-infrared light sources, the timing, detecting and processing circuitry of the prior patent applications, the present invention is primarily concerned with improvements in the body-mounted light emitting and light detecting components and with improved means for detachably mounting, light shielding and orienting such light source-detecting components on the body and in a manner designed to avoid excessive localized pressure and erroneous signal conditions.

The body-mounted invention apparatus is utilized in association with the near-infrared sources, timing, detecting and processing circuitry as well as the measuring techniques described in the prior patent applications. Thus, by making reference to the subject matter of the prior patent applications, it will be understood that the present invention apparatus facilitates the carrying out of a continuous, non-invasive, in vivo, in situ monitoring of the redox state of cytochrome a, $a_3$ in the body portion of interest by using the deep, diffuse, multiple-scattered light, reflectance technique and near-infrared radiation within the range of about 700–1300 nm as referred to and fully described in the prior patent applications. When the invention apparatus is applied to the head, for example, the light source and light detector components are spaced apart on the same side of the head and the light reflected and scattered back to the light source location is detected and used in the associated processing circuitry of the prior patent applications as a correction for skin blood volume changes. The present invention is particularly advantageous in minimizing light loss and also minimizing the establishment of localized pressure conditions and thus avoiding erroneous signal conditions. The present invention apparatus also further enhances the ability to discriminate between light scattered by the gray matter and light reflected from the white matter of the brain so as to provide a signal known to be indicative of the oxygen sufficiency in the gray matter of the brain.

With more specific reference to the actual structure employed in the improved light source-light detector body-mounted apparatus of the invention, there is provided a strap designed to be wrapped around a selected portion of the body, e.g., around the head, a limb or the torso, with the strap ends detachably secured for the purpose of supporting and orienting the light source, light detector, light shielding fiber optic and cable components of the invention. The mentioned strap mounts intermediate its length a block or section of resilient material adapted to conform to the shape of the body at the place of attachment. Such resilient material also serves as a means for encasing a pair of optical modules, the terminal ends of which serve as the required light source and light detector elements. These terminal ends are adapted to be detachably connected by quick disconnect couplings to a cable assembly used to transfer light or light-related signals between the body-mounted apparatus of the invention and external apparatus providing the light sources, the timing, detecting and processing circuitry in which the desired spectrophotometric measurements are actually made according to the techniques of the prior patent applications.

As compared to the light source-detector assembly of U.S. Pat. No. 4,321,930, the present invention provides an overall further simplified assembly. Additionally, improvements are provided by forming the light source and detector elements as uniquely constructed and separately mounted modules. The present invention also provides an improved means of light shielding obtained by using a double-sided, annular adhesive tape around the optical faces to improve both light shielding and body securement. Further, the present invention provides the option of using a vacuum sealing arrangement in conjunction with the strap arrangement of the present and prior patent applications to further enhance securement of the light source-detector elements to the body and whether of the fiber optic or electronic type.

All embodiments of the body-mounted invention apparatus provide means for detecting light reflected and scattered back from the location where the light first enters the body as well as separate means for detecting both scattered and reflected light at a point spaced from the light entry point. The invention apparatus also provides improved light shielding to prevent entry of ambient light or other extraneous light signals and also in a manner designed to avoid the establishment of harmful localized pressure at those points where the light enters and is detected. Thus, correction for skin blood volume changes is provided in all embodiments by means of monitoring the light reflected back at the point of light entry in conjunction with using the light reflected and scattered back to the second point for processing according to the techniques of the prior patent applications.

In all embodiments, the incoming light is transferred to the body-mounted apparatus of the invention by means of an optical cable connected to the light source element of the body-mounted apparatus. The corrective light reflected back from the body at the point where light from the light source enters the body as well as the measuring light reflected and scattered back to a point spaced from the light source are both detected and transmitted for processing by optical fiber means. The reflectance technique utilized by the present invention should be construed as the deep reflectance technique fully described in U.S. Pat. No. 4,321,930 and deemed incorporated herein by reference to avoid repetition.

DESCRIPTION OF THE DRAWINGS

FIG. 7 is a pictorial view of the body mountable light source-light detector apparatus according to a second embodiment of the invention utilizing vacuum attachment to the body.

FIG. 8 is an enlarged partial section view taken substantially along line 8—8 of FIG. 7.

FIG. 9 is a plan view of a vacuum adapted optical module suited to the apparatus of FIG. 7.

FIG. 10 is an end view of the optical module of FIG. 9 taken in the direction of line 10—10 of FIG. 9.

FIG. 11 is a section view taken substantially along line 11—11 of FIG. 9.

FIG. 12 is a section view taken substantially along line 12—12 of FIG. 9.

FIG. 13 is a plan view of a modified vacuum adapted optical module suited to the apparatus of FIG. 7.

FIG. 14 is a plan view of one side of an annular-shaped, double-sided, pressure sensitive tape useful with any of the optical modules of the invention but particularly with the optical modules of FIGS. 1–6.

BEST MODE FOR CARRYING OUT THE INVENTION

Figure 1:
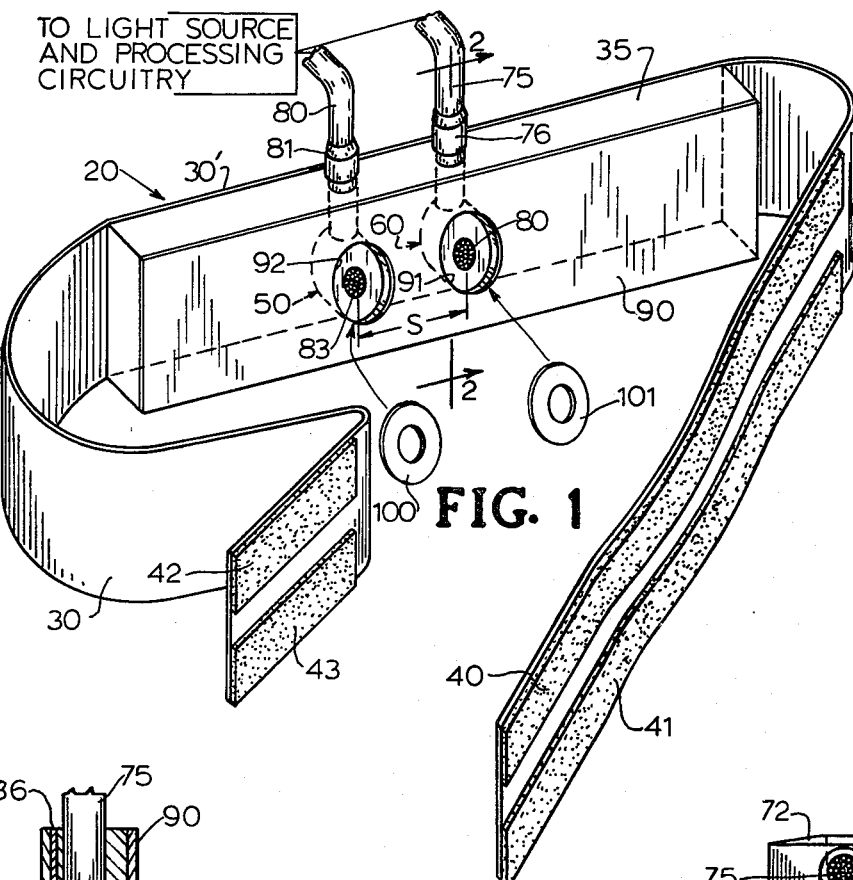
FIG. 1 is a pictorial view of the body mountable light source-light detector apparatus according to a first embodiment of the invention.

With the background description provided by the prior patent applications and which is deemed incorporated herein by reference to avoid repetition, it becomes evident that when the deep reflectance technique is followed, as described in U.S. Pat. No. 4,321,930, the means employed for introducing and implementing deep penetration of the near-infrared measuring and reference wavelengths at the point of light entry on the body, the means employed for collecting the directly and deeply reflected light at the point of light entry and the means for collecting the deeply penetrating light after being scattered and reflected from the organ, e.g., the brain or other body portion of interest, are of crucial and significant importance to obtaining meaningful measurements of the parameters desired. It is desirable, for example, that the light source-light detector assembly which is attached to the body be in a form adaptable to various body shapes such as associated with the head, a limb, or torso of a human or animal subject under observation. It has also been found critically important that light shielding associated with the body-mounted light source-detector assembly be effective both as to extraneous near-infrared as well as extraneous ambient light such that the light entering the body as well as the light detected will be only those wavelengths and only from those light sources intended to be associated with the measurements. Extraneous photon energy at the measuring location which might otherwise enter the body and affect the measurements is therefore desirably absorbed by means associated with the light source-detector assembly of the invention.

It has also become increasingly evident that the light source-detector assembly which attaches to the body must be in a form which avoids restricting local blood flow or any other tissue function in the area of observation so as to avoid erroneous signals. Additionally, it has been found desirable that the light source-detector elements have an improved body mounting arrangement that not only lends itself to shielding of extraneous light but also protects the elements as the mounting assembly changes to conform to the body shape at the area of observation. Another critical feature in the light source-detector element mounting structure is that the relative space between the light source and detector elements remain fixed during the measuring period and not be subject to alterations by physical changes in body geometry brought about by breathing, flexing of the body, trauma, and the like. Another major consideration is that the light source-detector assembly which is mounted on the body be in a form adapted to be quickly coupled and uncoupled to the timing, light source, detecting and processing circuitry typically located at least several feet away from the patient.

As another important consideration, it has been found highly desirable that the light source-detector assembly which attaches to the body be in a form lending itself to economical manufacture so as to be adapted to a single end use and useful as a disposable component. Considering the difficulty and cost of washing and sterilization, the possibility of transmitting diseases and the likelihood of contamination in surgical and accident cases in particular, the advantage of having a prepackaged, sterilized, single end use, disposable light source-detector assembly will be readily appreciated.

With the foregoing background information and desired characteristics and objectives in mind, the description next makes reference to the drawings to illustrate how the same are achieved in the improved body-mounted light source-light detector assembly of the invention.

Referring initially and principally to FIGS. 1–6, the improved light source-detector assembly 20 of the invention in a first embodiment basically comprises a base support strap 30, a module support 35 and embedded in support 35 a light source-detector module 50 and a light detector module 60.

Base support strap 30 is preferably formed of a tightly woven, elastic fabric such as found, for example, in elastic straps, stretchable belts, elastic fabric and the like. Strap 30 should preferable have an ability to stretch while providing sufficient flexibility to conform to the shape of the head, limb or torso of a human or animal subject under investigation. All surfaces of strap 30 are preferably black in color to assist in absorbing extraneous photon energy proximate to the observation area. The body strapping and unstrapping operation utilizing strap 30 is facilitated by employment of mating "Velcro" type strips 40–43 on the corresponding mating surfaces of strap 30 such that strap 30 can easily conform to the size and shape of body contour where the light source-detector assembly 20 is attached for monitoring purposes as fully described in the prior application.

Strap 30 includes an intermediate portion 30' adhered to an outer side surface of what will be referred to as the module support 35. A double-sided pressure sensitive tape 36 is used for this purpose and provides a means for both positive securement and ease of removal of the module support 35 when necessary for purposes of replacement or service.

Module support 35 is preferably formed of a material which is both resilient and deformable to a degree suited to the invention as described. Foam, e.g., silicone rubber represents a material which can be obtained from varying degrees of resiliency and is deemed suited for this purpose. Module support 35 is molded preferably with preformed cavities, not shown, suited to lightly gripping and encasing the pair of optical modules 50, 60 which are supported by module support 35 on strap 30.

While serving different functions, optical modules 50 and 60 are basically of similar construction and will be described in reference to FIGS. 2–6. Module 50, by way of example, comprises a hollow, circular-shaped housing 70 having a back cover plate 71 and a slightly tapered or slightly rounded front face 72 formed with a central aperture 73. A fiber bundle 75 couples through a quick disconnect optical coupling 76 and terminates with an L-shaped terminal end 79 having a ground optical face 80 located in the aperture 73. The void within housing 70 surrounding the L-shaped terminal end 79 is filled with an epoxy or similar hard setting compound to facilitate securement of the terminal end 79 within housing 70 and back cover plate 71 is suitably glued or otherwise secured in place after such assembly.

Terminal end 79 of fiber bundle 75 provides both a near-infrared light source terminal and a corrective detector terminal with selected fibers being employed for bringing light to the point of light entry and other randomly dispersed selected fibers being employed for collecting light reflected back directly from or near (1–3 mms) point of light entry. Since the manner in which such corrective and measured light sources operate and are processed are fully explained in the prior patent applications previously referred to, such description will not be repeated here to avoid repetition but is deemed incorporated by reference.

Module 60, as previously stated, employs a similar construction to that of module 50 and mounts a fiber bundle 80 through a quick disconnect optical coupling 81 having an L-shaped terminal end 82, not shown, with a ground optical face 83. Bundle 80 is used as a means for collecting the measured reflected light for processing as fully explained in the prior patent applications. Therefore, this aspect of the operation of the present invention apparatus will not be repeated here. Further, during the light measuring operation, modules 50 and 60 are mounted in module support 35 and the invention assembly 20 operates so as to maintain uniform the spacing "S" within the limits discussed in the prior patent applications.

Shielding of ambient light is deemed important especially when metabolic trends are being monitored and discrete changes are significant though small in value. Such shielding is provided by employing a layer of light shielding material 90 adhered to module support 35 and formed with suitable holes 91, 92 as illustrated to avoid covering the respective optical faces 80, 83.

As another aspect of the present invention, a pair of double-sided, annular-shaped, pressure-sensitive, adhesive tapes 100, 101 are employed on the respective modules 50, 60 and used to assist in providing the desired ambient light shielding. Tapes 100, 101 are preformed in the shape illustrated in FIG. 14 and typically have removable adhesive protective covering which, after removal, allows the respective tapes 100, 101 to be attached on one side to the respective modules 50, 60 while leaving the opposite side of the respective tapes 100, 101 exposed for securing to the respective body surfaces opposite the respective optical faces 80, 83.

In using the invention assembly 20 an optical gel is applied to each optical face 80, 83 and strap 30 is secured to the selected portion of the body so as to slightly compress the material forming module support 35 and bring the respective optical faces 80, 83 with the respective surrounding annular tapes 100, 101 into firm engagement with the body surfaces to maximize light contact and minimize leakage and loss of light at the points of light entry and exit. The slightly tapered or rounded surfaces on the respective front faces, e.g., face 72 of module 50, have been found to greatly facilitate such contact in view of the substantial variations in contour and surfaces found on the human body. Once the strap assembly 20 of the invention has been properly secured as previously explained in the prior patent applications referred to, appropriate optical and electrical circuits are established according to the prior patent applications and the present invention apparatus is used in the manner previously explained in such prior patent applications.

One of the important advantages of the improved strap assembly 20 of the present invention resides in the ability to perform the respective optical modules 50, 60 and assemble such optical modules with the module support 35 as a subassembly which can be quickly attached to the support strap 30 as previously explained and quickly coupled and uncoupled by means of the previously mentioned quick disconnect couplings 76, 81, all as previously described in reference to the first embodiment. Modules 50, 60 may be made of a suitable metal or plastic and molded or machined into the previously described form. Any suitable fabrication means may be employed to obtain the L-shaped configuration of the terminal ends of the respective optical bundles 75, 80 and to secure such optical bundles with respect to the respective optical modules 50, 60 so as to maintain the respective optical faces 80, 83 fixed relative to the respective modules 50, 60.

Referring next to FIGS. 7-13, there is described another embodiment of generally the same construction as the first embodiment but with the addition of a vacuum arrangement is employed to enhance light shielding and securement of the respective optical modules. As with the first embodiment, the assembly 140 of the second embodiment employs a base support strap 150 and a module support 155 secured to strap 150 and having a layer of light shielding material 156 with suitable openings for light passage as with the first embodiment. Within module support 155, there is embedded a pair of preformed optical modules 170, 180 of generally similar construction and also generally constructed similar to the previously described modules 50 and 60 but adapted for vacuum securement to the body.

Using module 170 by way of example, the hollow housing 181 mounts a fiber bundle 185 having an L-shaped terminal end 186. Terminal end 186 is optically coupled through a quick disconnect optical coupling 187 and terminates with a ground optical face 190 ground flush with a central aperture 191 formed in the slightly rounded or tapered front face 192. Housing 181 is formed with an internal air-tight chamber by means of back cover plate 193 which is secured in place to prevent air leakage and also by means of appropriate sealing against air leaks around fiber bundle 185 and optical face 190. The internal air-tight chamber within housing 181 is coupled to an air tube 194 connected through a quick disconnect coupling 195 to a suitable vacuum source, not shown. Front face 192 of housing 181 is formed with four elliptical depressions 200 which communicate through corresponding holes 201 to the vacuum chamber within housing 181 to which the vacuum supply air tube 194 is connected. In an alternative embodiment shown in FIG. 13, the elliptical depressions 200 are interconnected by other depressions 202 to increase the total body surface exposed to the vacuum effect.

Module 180, in a similar manner and utilizing a generally similar construction, mounts an optical bundle 205 connected through coupling 206 and having an L-shaped terminal, not shown, with an optical face 210. Module 180 also mounts a vacuum support air tube 215 coupled through a quick disconnect coupling 216 to the same vacuum source supplying vacuum air tube 194.

Bundle 185 serves the same function as bundle 75 of the first embodiment and bundle 205 serves the same function as bundle 80 of the first embodiment. Therefore, this part of the description will not be repeated.

In using the strap assembly 140 of the second embodiment, the required optical transmission and vacuum circuits are established and optical gel is applied to the respective optical faces 190, 210. The strap 150 is then suitable secured so as to place the respective housing front faces, e.g., face 192, and respective optical faces 190, 210 in suitably body contact and also to place the respective vacuum supplied recesses 200 directly over and surrounding the body surfaces serving as points of light entry and exit. Where increased vacuum effect is desired because of the nature of the body surface to which the invention apparatus is being attached, the alternative module construction illustrated in FIG. 13 increases the vacuum effect and thereby increases the vacuum assisted securement to the body. Thus, in conjunction with the resilient pressing effect afforded by strap 150 and module support 155, there is provided an improved auxiliary vacuum assisted means for obtaining improved light shielding and securement of the strap assembly 140 according to the second embodiment. As with the first embodiment, the resilient and deformable character of the material chosen for module support 155 allows the thickness of the module support 155, as viewed in FIG. 8, to contract when strap 150 is applied and suitably secured by use of the appropriate "Velcro" straps 220–223. With the optical module support 155 resiliently compressed in this fashion, with an optical gel applied to the respective optical faces 190, 210 and with the appropriate vacuum applied to the respective modules 170, 180, it can be seen that a substantially improved and effective optical coupling is secured. Further, as with the first embodiment, the optical modules 170, 180 can be prefabricated and installed in appropriate molded recesses in module support 155 as a subassembly for quick connection to the light source, light processing and vacuum equipment. Further, annular, double-sided, pressure-sensitive tapes as previously described may be employed around the respective optical faces to enhance securement when not using the vacuum. However, the vacuum securement is particularly advantageous when measuring wert surfaced portions of the body as for example in open heart surgery.

While not illustrated, it will also be appreciated that the illustrated optical modules may be formed with continuous fiber bundles leading to the light source and processing circuitry so as to avoid the use of the illustrated quick disconnect couplings.

Also to be recognized is that the described vacuum arrangement lends itself to use with optical modules fitted with photo-detector, i.e., electronic type light sensors as in our prior patent application Ser. No. 188,578. Thus, a new and versatile means of securement by vacuum is provided.

Figure 2:
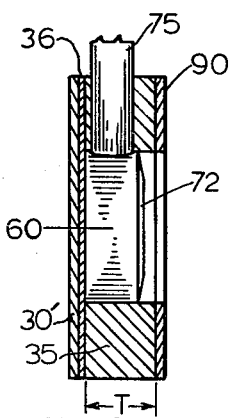
FIG. 2 is an enlarged partial section view taken substantially along line 2—2 of FIG. 1.
Figure 3:
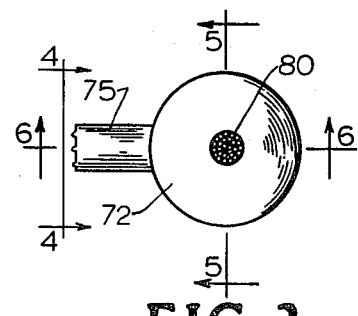
FIG. 3 is a plan view of an optical module suited to the apparatus of FIG. 1.
Figure 4:
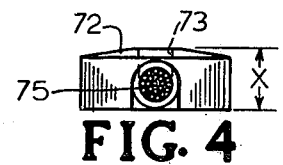
FIG. 4 is an end view of the optical module of FIG. 3 taken in the direction of line 4—4 of FIG. 3.
Figure 5:
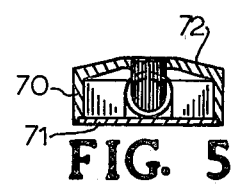
FIG. 5 is a section view taken substantially along line 5—5 of FIG. 3.
Figure 6:
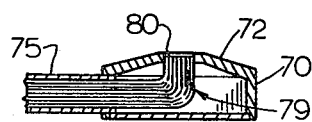
FIG. 6 is a section view taken substantially along line 6—6 of FIG. 3.

Another feature to be recognized in the illustrated embodiments as best seen in reference to FIG. 2 is that the thickness T of the module support material is purposely made larger than the overall thickness X (FIG. 4) of the optical modules. This allows the module support foam material 35 to effectively slide on the respective optical modules and be slightly compressed during application to the body and which assists in holding the respective modules properly positioned.

We claim:

1. In a spectrophotometric reflectance apparatus for measuring in situ, in vivo, non-invasively, atraumatically, harmlessly, rapidly and continuously a local metabolic oxygen dependent activity of a selected portion of the body where such activity bears a measurable relation to an oxygen dependent absorption characteristic of the selected portion for a particular wavelength of light transmitted therethrough having:

(a) circuitry means including:
  (i) a plurality of near-infrared light sources located external of the body and having light emissions of different wavelengths in the 700–1300 nanometer spectral range and of an intensity below the level damaging to the body and said selected portion but sufficient to be detectable by a light sensor after transmission through any skin, bone and tissue included in an optical transmission-reflectance path including said selected portion thereof and extending for several centimeters between selected points of light entry and exit laterally spaced several centimeters apart and located on contiguous skin surface areas of the body and after scattering in and deep reflectance from said selected portion along said path, said emissions including at least one measuring wavelength and at least one reference wavelength within said spectral range, each said measuring wavelength being selected such that said selected portion exhibits a selected absorption therefore, the extent of which is dependent upon a specific state of a local metabolic, oxygen dependent activity of said selected portion; and
  (ii) means operatively associated with said light sources to produce emissions representing at least one said measuring wavelength and at least one said reference wavelength within said spectral range for transmission along said path to said selected portion and at levels of intensity below that which would be damaging to the body and said selected portion;

(b) first optical cable means providing a bundle of optical fibers with selected fibers connected for receiving, transmitting and directing the output light emissions of said light sources at said measuring and reference wavelengths to a selected light entry point proximate said body and other selected fibers connected for receiving deeply penetrating light emissions reflected directly back from any skin, bone and tissue at or within a few millimeters of said selected point of light entry and coupling such emissions to a processing means;

(c) second optical cable means providing a bundle of optical fibers adapted for receiving deeply penetrating light emissions reflected and scattered to said selected point of light exit from said selected portion of said body and coupling such exiting light emissions to a processing means; and (d) processing means operatively associated with said circuitry means adapted to produce from the outputs of said first and second optical cable means an electrical output signal corrected for changes in blood volume of said skin, bone and tissue during the measuring cycle and representing the difference in absorption of said measuring and reference wavelengths by said selected body portion as a function of the state of said local metabolic oxygen dependent activity and further adapted to convert said electrical output signal to a signal providing a substantially continuous and rapid measure of said activity;

(e) an improved detachable, body mountable apparatus associated with said circuitry, coupling and processing means comprising:
  (i) a flexible, elongated support member adapted to be releasably secured to the body proximate a said selected portion of the body having a selected set of said light entry and exit points, said support member being adapted to provide ambient light shielding over said light entry and exit points and to conform to the curvature and shape of the body at the location thereof;
  (ii) a mounting structure secured to said support member and adapted to deform in shape in correspondence with the curvature assumed by said support member when secured to the body;
  (iii) a first preformed optical module mounted in said structure and providing a hollow housing enclosing first right angled light guide means formed by a bundle of optical fibers optically coupled to said first optical cable means and having an optical face centered in a slightly tapered outer face of said housing and adapted to be mated in a substantially pressed fit relation with said selected point of light entry utilizing selected fibers of said bundle for entry of light in said wavelengths to be transmitted, deeply reflected and scattered along said path and to said selected portion and other selected fibers for receiving deeply penetrating light emissions reflected directly back from any skin, bone and tissue at or within a few millimeters of said selected point of light entry;

(iv) a second preformed optical module mounted in said mounting structure and providing a second hollow housing enclosing second right angled light guide means formed by a bundle of optical fibers optically coupled to said second optical cable means and having a second optical face centered in a slightly tapered outer face of said second housing and spaced several centimeters away from said first optical face and adapted to be mated in a substantially pressed fit relation with said selected point of light exit for receiving deeply penetrating light emissions reflected and scattered to said selected point of light exit from said selected portion of said body.

2. In an apparatus as claimed in claim 1 wherein each said optical module includes openings in the respective outer faces of the respective housings thereof surrounding the respective optical faces thereof and means communicating said openings to a vacuum source whereby securement of said optical faces to the respective points of light entry and exit is enhanced by a vacuum assisted pull on the skin surrounding said points.

3. In an apparatus as claimed in claim 1 including annular shaped, double-faced, pressure-sensitive adhesive tapes adhered to the respective outer faces of said housings surrounding the respective optical faces and adapted for securement to the skin surrounding said points.

4. In an apparatus as claimed in claim 1 wherein said mounting structure is detachably secured to said support member.

5. An improved detachable, body mountable apparatus for association with spectrophotometric circuitry, coupling and processing means comprising:

(i) a flexible, elongated support member adapted to be releasably secured to the body proximate a said selected portion of the body having a selected set of light entry and exit points, said support member being adapted to provide ambient light shielding over said light entry and exit points and to conform to the curvature and shape of the body at the location thereof;

(ii) a mounting structure secured to said support member and adapted to deform in shape in correspondence with the curvature assumed by said support member when secured to the body;

(iii) a first preformed optical module mounted in said structure and providing a hollow housing enclosing first right angled light guide means formed by a bundle of optical fibers optically coupled to external optical cable means and having a first optical light emitting face positioned in an outer face of said housing having openings therethrough and adapted to be mated in a substantially pressed fit relation with said selected point of light entry utilizing fibers of said bundle for entry of light in selected wavelengths to be transmitted, deeply reflected and scattered along said path and to said selected portion and further enclosing a first light detector means coupled to a processing means and having a first light receiving face positioned in said outer face of said housing for receiving and processing deeply penetrating light emissions reflected directly back from any skin, bone and tissue at or within a few millimeters of said selected point of light entry;

(iv) a second preformed optical module mounted in said mounting structure and providing a second hollow housing enclosing a second light detector means coupled to processing means and having a second light receiving face positioned in an outer face of said second housing and spaced several centimeters away from said first optical face, said outer face of said second housing having openings therethrough and adapted to be mated in a substantially pressed fit relation with said selected point of light exit for receiving and processing deeply penetrating light emissions reflected and scattered to said selected point of light exit from said selected portion of said body; and (v) means communicating said face openings to a vacuum source whereby securement of said optical faces to the respective points of light entry and exit may be enhanced by a vacuum assisted pull on the skin surrounding said points.

* * * * *

UNITED STATES PATENT AND TRADEMARK OFFICE
CERTIFICATE OF CORRECTION

PATENT NO. : 4,380,240
DATED : April 19, 1983
INVENTOR(S) : Frans F. Jobsis; Johannes H. Keizer; and Ronald F. Overaker It is certified that error appears in the above—identified patent and that said Letters Patent is hereby corrected as shown below:

Col. 1, line 38, "a, a$_3$" should be --$\underline{a}$, $\underline{a}_3$--.

Col. 1, line 39, "c" should be --$\underline{c}$--.

Col. 3, line 4, "a, a$_3$" should be --$\underline{a}$, $\underline{a}_3$--.

Col. 6, line 31, "from" should be --with--.

Col. 7, line 50, "perform" should be --preform--.

Col. 8, line 51, "suitable" should be --suitably--.

Col. 8, line 53, "suitably" should be --suitable--.

Col. 9, line 19, "wert" should be --wet--.

Signed and Sealed this

Sixteenth Day of August 1983

[SEAL]

Attest:

GERALD J. MOSSINGHOFF

Attesting Officer

Commissioner of Patents and Trademarks